US012797335B2

(12) United States Patent
Brams et al.

(10) Patent No.: US 12,797,335 B2
(45) Date of Patent: Nov. 17, 2026

(54) TRIMODAL, PRECISION-TIMED RELEASE TABLET

(71) Applicant: CINGULATE THERAPEUTICS LLC, Kansas City, KS (US)

(72) Inventors: Matthew Brams, Kansas City, KS (US); Arthur Straughn, Kansas City, KS (US); Shane Schaffer, Kansas City, KS (US)

(73) Assignee: Cingulate Therapeutics LLC, Kansas City, KS (US)

( * ) Notice: Subject to any disclaimer, the term of this patent is extended or adjusted under 35 U.S.C. 154(b) by 211 days.

(21) Appl. No.: 18/838,775

(22) PCT Filed: Feb. 15, 2023

(86) PCT No.: PCT/US2023/013139
§ 371 (c)(1),
(2) Date: Aug. 15, 2024

(87) PCT Pub. No.: WO2023/158694
PCT Pub. Date: Aug. 24, 2023

(65) Prior Publication Data
US 2025/0177310 A1 Jun. 5, 2025

Related U.S. Application Data

(60) Provisional application No. 63/310,677, filed on Feb. 16, 2022.

(51) Int. Cl.

| | |
|---|---|
| ***A61K 9/24*** | (2006.01) |
| ***A61K 9/20*** | (2006.01) |
| ***A61K 31/506*** | (2006.01) |

(52) U.S. Cl.
CPC ............ *A61K 9/209* (2013.01); *A61K 9/2009* (2013.01); *A61K 9/2031* (2013.01); *A61K 9/205* (2013.01);
(Continued)

(58) Field of Classification Search
CPC .... A61K 9/209; A61K 9/2009; A61K 9/2031; A61K 9/205; A61K 9/2054; A61K 9/2059; A61K 31/506; A61P 25/22
See application file for complete search history.

(56) References Cited

U.S. PATENT DOCUMENTS

| | | | |
|---|---|---|---|
| 4,728,512 | A | 3/1988 | Mehta et al. |
| 5,837,284 | A | 11/1998 | Mehta et al. |

(Continued)

FOREIGN PATENT DOCUMENTS

| | | | |
|---|---|---|---|
| CN | 1977845 A | 6/2007 | |
| EP | 0313535 B1 | 7/1994 | |

(Continued)

OTHER PUBLICATIONS

"ADHD & Patient Experience"; Cingulate Press Release, first published online Jul. 4, 2022 (https://web.archive.org/web/20220704034125/https://www.cingulate.com/technology/innovation-in-adhd). (Year: 2022).*

(Continued)

*Primary Examiner* — Jeffrey T. Palenik
(74) *Attorney, Agent, or Firm* — Mintz, Levin, Cohn, Ferris, Glovsky and Popeo, P.C.

(57) ABSTRACT

A trimodal, precision-timed release tablet that delivers a trimodal release profile is provided. The tablet includes at least three immediate release components of buspirone where the release times are controlled by an erosion barrier layer.

15 Claims, 2 Drawing Sheets

(52) U.S. Cl.
CPC .......... *A61K 9/2054* (2013.01); *A61K 9/2059* (2013.01); *A61K 31/506* (2013.01)

(56) References Cited

U.S. PATENT DOCUMENTS

| | | | |
|---|---|---|---|
| 5,945,123 | A | 8/1999 | Hermelin |
| 6,210,705 | B1 | 4/2001 | Mantelle et al. |
| 6,217,904 | B1 | 4/2001 | Midha et al. |
| 6,228,398 | B1 | 5/2001 | Devane et al. |
| 6,322,819 | B1 | 11/2001 | Burnside et al. |
| 6,333,050 | B2 | 12/2001 | Wong et al. |
| 6,340,476 | B1 | 1/2002 | Midha et al. |
| 6,344,215 | B1 | 2/2002 | Bettman et al. |
| 6,348,211 | B1 | 2/2002 | Mantelle et al. |
| 6,419,960 | B1 | 7/2002 | Krishnamurthy et al. |
| 6,458,384 | B2 | 10/2002 | Jaenicke et al. |
| 6,555,127 | B2 | 4/2003 | Steiner |
| 6,555,136 | B2 | 4/2003 | Midha |
| 6,638,533 | B2 | 10/2003 | Krsek |
| 6,673,367 | B1 | 1/2004 | Goldenheim et al. |
| 6,730,321 | B2 | 5/2004 | Ting et al. |
| 6,730,325 | B2 | 5/2004 | Devane et al. |
| 6,793,936 | B2 | 9/2004 | Devane et al. |
| 6,902,742 | B2 | 6/2005 | Devane et al. |
| 6,913,768 | B2 | 7/2005 | Couch et al. |
| 6,919,373 | B1 | 7/2005 | Lam et al. |
| 6,930,129 | B2 | 8/2005 | Lam et al. |
| 7,048,945 | B2 | 5/2006 | Percel et al. |
| 7,083,808 | B2 | 8/2006 | Goldenheim et al. |
| 7,132,072 | B2 | 11/2006 | Ozeki et al. |
| 7,141,250 | B2 | 11/2006 | Oshlack et al. |
| 7,223,735 | B2 | 5/2007 | Mickle et al. |
| 7,247,318 | B2 | 7/2007 | Krishnamurthy et al. |
| 7,431,944 | B2 | 10/2008 | Mehta et al. |
| 7,438,930 | B2 | 10/2008 | Krishnamurthy et al. |
| 7,569,274 | B2 | 8/2009 | Besse et al. |
| 7,581,941 | B2 | 9/2009 | Harada et al. |
| 7,611,728 | B2 | 11/2009 | Kidane et al. |
| 7,660,948 | B2 | 2/2010 | Bates et al. |
| 7,674,480 | B2 | 3/2010 | Fleshner-Barak et al. |
| 7,687,466 | B2 | 3/2010 | Mickle et al. |
| 7,687,467 | B2 | 3/2010 | Mickle et al. |
| 7,700,561 | B2 | 4/2010 | Mickle et al. |
| 7,713,455 | B2 | 5/2010 | Ozeki et al. |
| 7,713,936 | B2 | 5/2010 | Mickle et al. |
| 7,718,619 | B2 | 5/2010 | Mickle et al. |
| 7,723,305 | B2 | 5/2010 | Mickle et al. |
| 7,771,707 | B2 | 8/2010 | Hirsh et al. |
| 7,772,222 | B2 | 8/2010 | Mickle |
| 7,811,488 | B2 | 10/2010 | Ozeki et al. |
| 7,988,993 | B2 | 8/2011 | Dixit et al. |
| 8,062,667 | B2 | 11/2011 | Mehta et al. |
| 8,101,661 | B2 | 1/2012 | Mickle |
| 8,124,653 | B2 | 2/2012 | Matalon et al. |
| 8,163,798 | B2 | 4/2012 | Gupta et al. |
| 8,211,905 | B1 | 7/2012 | King et al. |
| 8,232,315 | B2 | 7/2012 | Lee et al. |
| 8,252,327 | B2 | 8/2012 | Dixit et al. |
| 8,318,210 | B2 | 11/2012 | Tengler et al. |
| 8,323,691 | B2 | 12/2012 | Geerke et al. |
| 8,329,720 | B1 | 12/2012 | King et al. |
| 8,465,765 | B2 | 6/2013 | Mehta et al. |
| 8,465,768 | B2 | 6/2013 | Park et al. |
| 8,846,100 | B2 | 9/2014 | Shojaei et al. |
| 9,833,412 | B2 | 12/2017 | Toneguzzo et al. |
| 10,005,432 | B2 | 6/2018 | Polocoser et al. |
| 10,561,618 | B2 | 2/2020 | Hansen et al. |
| 2001/0055613 | A1 | 12/2001 | Burnside et al. |
| 2003/0050620 | A1 | 3/2003 | Odidi et al. |
| 2003/0170181 | A1 | 9/2003 | Midha |
| 2003/0194439 | A1 | 10/2003 | Midha et al. |
| 2004/0219213 | A1 | 11/2004 | Burnside et al. |
| 2004/0220277 | A1 | 11/2004 | Couch et al. |
| 2004/0241234 | A1 | 12/2004 | Vilkov |
| 2005/0181049 | A1 | 8/2005 | Dong et al. |
| 2006/0073189 | A1 | 4/2006 | Pinney et al. |
| 2006/0153918 | A1 | 7/2006 | Lerner et al. |
| 2006/0204575 | A1 | 9/2006 | Feng et al. |
| 2006/0210633 | A1 * | 9/2006 | Dharmadhikari .... A61K 9/0004 424/473 |
| 2007/0071806 | A1 | 3/2007 | McCarty |
| 2007/0154547 | A1 | 7/2007 | Flanner et al. |
| 2007/0225334 | A1 | 9/2007 | Rosenzweig-Lipson |
| 2007/0243252 | A1 | 10/2007 | Heinicke |
| 2007/0264323 | A1 | 11/2007 | Shojaei et al. |
| 2007/0292508 | A1 | 12/2007 | Szamosi et al. |
| 2008/0008659 | A1 | 1/2008 | Guimberteau et al. |
| 2008/0020041 | A1 | 1/2008 | Ayres |
| 2008/0045588 | A1 | 2/2008 | Gant et al. |
| 2008/0069872 | A1 | 3/2008 | Rubio et al. |
| 2008/0075769 | A1 | 3/2008 | Poestges et al. |
| 2008/0248107 | A1 | 10/2008 | Pilgaonkar et al. |
| 2008/0274194 | A1 | 11/2008 | Miller et al. |
| 2009/0004285 | A1 | 1/2009 | Yu et al. |
| 2009/0028941 | A1 | 1/2009 | Cowles et al. |
| 2009/0053310 | A1 | 2/2009 | Pilgaonkar et al. |
| 2009/0143761 | A1 | 6/2009 | Cantor et al. |
| 2009/0220611 | A1 | 9/2009 | Dargelas et al. |
| 2009/0220613 | A1 | 9/2009 | Odidi et al. |
| 2009/0297597 | A1 | 12/2009 | Liversidge et al. |
| 2009/0304787 | A1 | 12/2009 | Odidi et al. |
| 2010/0005781 | A1 | 1/2010 | Schweizer |
| 2010/0092553 | A1 | 4/2010 | Guimberteau et al. |
| 2010/0104621 | A1 | 4/2010 | Waldo |
| 2010/0137271 | A1 | 6/2010 | Chen et al. |
| 2010/0166864 | A1 | 7/2010 | Gadre et al. |
| 2010/0172916 | A1 | 7/2010 | Gant et al. |
| 2010/0256746 | A1 | 10/2010 | Taylor et al. |
| 2010/0266701 | A1 | 10/2010 | Guimberteau et al. |
| 2011/0009669 | A1 | 1/2011 | Mickle et al. |
| 2011/0118310 | A1 | 5/2011 | Khetani |
| 2011/0207718 | A1 | 8/2011 | Bird |
| 2011/0223247 | A1 | 9/2011 | Park et al. |
| 2012/0225118 | A1 | 9/2012 | Chen et al. |
| 2012/0276017 | A1 | 11/2012 | Lickrish et al. |
| 2012/0295893 | A1 | 11/2012 | Peled et al. |
| 2012/0302590 | A1 | 11/2012 | Bhide et al. |
| 2013/0011478 | A1 | 1/2013 | Chaturvedi |
| 2013/0017262 | A1 | 1/2013 | Mullen et al. |
| 2013/0022646 | A1 | 1/2013 | Rudnic et al. |
| 2013/0022676 | A1 | 1/2013 | Mullen et al. |
| 2013/0022677 | A1 | 1/2013 | Mullen et al. |
| 2013/0022678 | A1 | 1/2013 | Dixit et al. |
| 2013/0035315 | A1 | 2/2013 | Hanna et al. |
| 2013/0039960 | A1 | 2/2013 | Desai |
| 2013/0053414 | A1 | 2/2013 | Zeldis et al. |
| 2013/0079415 | A1 | 3/2013 | Vergnault et al. |
| 2013/0195934 | A1 | 8/2013 | Gupta et al. |
| 2013/0209562 | A1 | 8/2013 | Lam et al. |
| 2013/0236554 | A1 | 9/2013 | Tengler et al. |
| 2013/0243871 | A1 | 9/2013 | Mcmahen et al. |
| 2013/0289061 | A1 | 10/2013 | Bhide et al. |
| 2013/0295170 | A1 | 11/2013 | Dordunoo |
| 2014/0011842 | A1 | 1/2014 | Scicinski et al. |
| 2014/0023705 | A1 | 1/2014 | Tengler et al. |
| 2014/0030322 | A1 | 1/2014 | Bosse et al. |
| 2014/0030348 | A1 | 1/2014 | Tengler et al. |
| 2014/0037728 | A1 | 2/2014 | Tengler et al. |
| 2014/0050797 | A1 | 2/2014 | Venkatesh et al. |
| 2014/0072644 | A1 | 3/2014 | Guimberteau et al. |
| 2014/0072645 | A1 | 3/2014 | Tengler et al. |
| 2014/0099361 | A1 | 4/2014 | Krishnamurthy et al. |
| 2014/0112996 | A1 | 4/2014 | Tengler et al. |
| 2014/0120061 | A1 | 5/2014 | Roth et al. |
| 2014/0142140 | A1 | 5/2014 | Bird |
| 2014/0171510 | A1 | 6/2014 | Mickle |
| 2014/0212461 | A1 | 7/2014 | Lickrish et al. |
| 2014/0212483 | A1 | 7/2014 | Lickrish et al. |
| 2014/0256823 | A1 | 9/2014 | McCarty |
| 2014/0302141 | A1 | 10/2014 | Toneguzzo et al. |
| 2016/0250148 | A1 | 9/2016 | Brams et al. |
| 2020/0146991 | A1 | 5/2020 | Brams et al. |
| 2024/0238208 | A1 | 7/2024 | Brams et al. |

(56) References Cited

U.S. PATENT DOCUMENTS

FOREIGN PATENT DOCUMENTS

| | | | | | |
|---|---|---|---|---|---|
| EP | 2368546 | A2 | | 9/2011 | |
| JP | 2002527468 | A | | 8/2002 | |
| JP | 2004501190 | A | | 1/2004 | |
| JP | 2010527468 | A | | 8/2010 | |
| JP | 2013530952 | A | | 8/2013 | |
| JP | 2017532363 | A | | 11/2017 | |
| JP | 2018506590 | A | | 3/2018 | |
| WO | 0200213 | A1 | | 1/2002 | |
| WO | WO-2004108067 | A2 | * | 12/2004 | ............ A61M 31/00 |
| WO | 2007133203 | A1 | | 11/2007 | |
| WO | WO-2013030726 | A1 | * | 3/2013 | ......... A61K 31/5517 |
| WO | 2014174387 | A1 | | 10/2014 | |
| WO | 2016065481 | A1 | | 5/2016 | |

OTHER PUBLICATIONS

Extended European Search Report issued in European Application 23756849.8, mailed on Jan. 23, 2026, 8 pages.

(March 17, 2026) “Cingulate’s Precision Timed Release (PTR) Platform Technology”, Cingulate® Technology, 2 pages.

Extended European Search Report issued in European Application 25223778.9, mailed on Apr. 22, 2026, 6 pages.

Extended European Search Report issued in European Application 16756485.5, mailed on Sep. 20, 2018, 6 pages.

International Search Report and Written Opinion Issued in PCT Application No. PCT/US2022/028550, mailed on Aug. 11, 2022, 11 pages.

International Search Report and Written Opinion received in PCT Application No. PCT/US2016/019877, mailed on May 20, 2016, 9 pages.

Bodmeier, Roland (1997) “Tableting of Coated Pallets”, European Journal of Pharmaceutics and Biopharmaceutics, 43:1-8.

Chang et al. (1991) “The Effect of Various Polymeric Coating Systems on the Dissolution and Tableting Properties of Potassium Chloride Microcapsules”, International Journal of Pharmaceutics, 70:261-270.

Dwibhashyam et al. (September-Oct. 2008) “Key Formulation Variables in Tableting of Coated Pellets”, Indian Journal of Pharmaceutical Sciences, 70(5):555-564 (13 pages).

Greenhill et al. (2001) “Correlations between Motor Persistence and Plasma Levels in Methylphenidate-Treated Boys with ADHD”, International Journal of Neuropsychopharmacology, 4:207-215.

Silva et al. (2018) “Pharmacoscintigraphic and Pharmacokinetic Analysis of CTx-1301, a Novel Tri-modal Oral Formulation for Release of Dexmethylphenidate in Healthy Adults”, https://www.cingulate.com/static-files/049389ce-6e57-4017-a021-5ee3ca84239c#:~:text=Results%3A%20The%20two%20CTx%2D1301,XR%C2%AE%20(3.0%20hours), 1 page.

* cited by examiner

TRIMODAL, PRECISION-TIMED RELEASE TABLET

CROSS-REFERENCE TO RELATED APPLICATIONS

This present application is a U.S. national stage application under 35 U.S.C. 371 of International Patent Application No. PCT/US2023/013139 filed on Feb. 15, 2023, which claims priority to U.S. Provisional Patent Application Ser. No. 63/310,677 filed on Feb. 16, 2022. The content of the above-referenced application is herein expressly incorporated by reference in its entirety, including any drawings.

BACKGROUND OF THE INVENTION

Buspirone is an immediate release dosage form administered up to three times a day for the treatment of generalized anxiety disorder (GAD). There remains a significant need for a single daily dosage form to achieve improved efficacy and patient compliance. Past efforts to achieve a multiple-release single-dosage form of buspirone have failed. Buspirone, Selective Serotonin Reuptake Inhibitors (SSRI's), and Selective Non-Serotonin Reuptake Inhibitors (SNRI's) are the only first-line therapies for the treatment of GAD. Today, buspirone is adminstered two to three times per day at intervals of 4, 6, 8, or 12 hours posing significant challenges to patients, and failure to adhere to such a regimen leads to suboptimal results.

There remains a need for a single, once-daily oral dosage form that delivers multiple-releases of buspirone in a manner that provides a safe and effective therapeutic response lasting the patient's day.

SUMMARY OF THE INVENTION

A trimodal, precision-timed release tablet that delivers a three release profile is provided herein. According to one embodiment, the tablet includes three release components inside the final tablet. By providing a single tablet having multiple release components, the dosing frequency is decreased, patient compliance is increased, and precise blood levels of the active pharmaceutical ingredient (API; e.g., the anti-anxiety drug or the anxiolytic) are precisely achieved over an extended period of time. Further benefits include improvements in efficacy.

The trimodal, precision-timed release tablet disclosed herein provides a pharmaceutically precise amount of buspirone initially to the patient to achieve the desired pharmacological response via a first release component and deliver the remaining predetermined amounts of buspirone via second and third release components to maintain the effective therapeutic pharmacological activity for a period of time in excess of the time expected from a single, immediate-release drug formulation.

According to one embodiment, the tablet provides a trimodal, precision-timed release tablet for oral administration of buspirone or pharmaceutically acceptable salt thereof comprising three release components.

In an embodiment, the first release component comprises (i) about 15% w/w to about 25% w/w of buspirone as a first precision-timed release, wherein about 10% to about 50% of the total buspirone in the tablet is released at time zero following oral administration of the tablet to a patient (ii) about 1% w/w to about 5% w/w of croscarmellose sodium, (iii) about 65% w/w to about 78% w/w of microcrystalline cellulose, (iv) about 0.5% w/w to about 1.5% w/w of magnesium stearate (v) about 2.0% w/w to about 6% w/w of sodium starch glycolate; and (vi) about 0.25% w/w to about 0.75% w/w of colloidal silicon dioxide.

In an embodiment, the second release component comprises (i) about 15% w/w to about 25% w/w of buspirone as a second precision-timed release of about 30% to about 40% of the total buspirone in the tablet released from about 3 to about 5 hours following oral administration of the tablet to a patient, (ii) about 1% w/w to about 4% w/w of croscarmellose sodium, (iii) about 65% w/w to about 78% w/w of microcrystalline cellulose, (iv) about 0.5% w/w to about 1.5% w/w of magnesium stearate (v) about 2.0% w/w to about 6% w/w of sodium starch glycolate; and (vi) about 0.25% w/w to about 0.75% w/w of colloidal silicon dioxide.

In an embodiment, the third release component comprises (i) about 15% w/w to about 25% w/w of buspirone as a third precision-timed release of about 10% to about 40% of the total buspirone in the tablet released about 6 to about 12 hours following oral administration of the tablet to a patient, (ii) about 1% w/w to about 4% w/w of croscarmellose sodium, (iii) about 65% w/w to about 78% w/w of microcrystalline cellulose, (iv) about 0.5% w/w to about 1.5% w/w of magnesium stearate (v) about 2.0% w/w to about 6% w/w of sodium starch glycolate; and (vi) about 0.25% to about 0.75% of colloidal silicon dioxide.

According to one embodiment, the tablet includes a first release component having a first precision-timed release of buspirone of about 10% to about 50% of the total busprione in the tablet; a second release component having a second precision-timed release of buspirone of about 30% to about 40% of the total buspirone in the tablet; and a third release component having a third precision-timed release of buspirone of about 10% to about 40% of the total amount of buspirone in the tablet, so that the total dose or label claim of the buspirone in the final tablet is 100%.

According to one embodiment, the tablet is structured such that the first release component is positioned on the exterior of the tablet and on an outer erosion barrier layer; the second release component is positioned between the outer erosion barrier layer and an inner erosion barrier layer such that it is surrounded by the outer and inner erosion barrier layers; and the third release component is positioned at the center of the tablet and surrounded by the inner erosion barrier layer. In embodiments, the release components are positioned substantially similar to FIG. 2.

By positioning the first release component on the exterior of the tablet, the first precision-timed release of buspirone can be released within about 5 minutes to about 45 minutes after administration to a patient. In embodiments, the first precision-timed release will be 90% complete within 30 minutes. By surrounding the second and third release components with erosion barrier layers, the second and third precision-timed releases of buspirone can be delayed releases. The delivery of the second precision-timed release of buspirone can be delayed until about 3 to about 5 hours following administration of the tablet to a patient. The delivery of the third precision-timed release of buspirone can be delayed until about 6 to about 12 hours following oral administration of the tablet to a patient.

The outer and inner erosion barrier layers each comprise about 30% to about 50% by weight of glyceryl behenate, about 40% to about 60% by weight of two or more grades of low-substituted hydroxypropyl cellulose (L-HPC), and about 4% to about 8% by weight of hydroxypropyl cellulose. The two or more grades of L-HPC can be LH-21 and LH-32.

The tablet described herein is to be administered orally in a pharmaceutically effective amount to a patient once daily to treat or prevent a variety of disorders, conditions, and diseases. According to one embodiment, administration of at least one anxiolytic may be carried out in order to treat any disorder, condition, or disease for which an anxiolytic is generally indicated in the present or the future. Such disorders, conditions, and diseases include, for example, generalized anxiety disorder.

The tablet described herein can be an effective method to provide the therapeutic duration of buspirone for the entire day and offer compelling advantages for safety and tolerability.

DETAILED DESCRIPTION OF THE INVENTION

As used in the specification and the appended claims, the singular forms "a," "an," and "the" include plural referents unless the context clearly dictates otherwise.

"Active ingredient" and "pharmacologically active ingredient" are used herein to refer to a chemical material or compound which induces a desired pharmacologic effect.

"Anxiolytic" as used herein refers to any active pharmaceutical ingredient administered to reduce anxiety. Anxiolytic may also refer to "anti-anxiety medication," which treat anxiety related disorders and related psychological and physical symptoms. In embodiments, anti-anxiety medications may include but are not limited to benzodiazepines, buspirone, meprobamate, and hyroxyzine.

"Buspirone" as used herein, refers to 8-[4-[4-(2-pyrimidinyl)-1-piperazinyl]butyl]-8-azaspiro[4.5]decane-7,9-dione. Buspirone also includes all pharmaceutically acceptable salts, metabolites and prodrugs thereof, such as buspirone hydrochloride. The hydrochloride salt is a white crystalline, water soluble compound. Busprione is sold under the trade names BUSPAR® and NAMANSPIN®.

"Day" as used herein, refers to 16 to 24 hours. In embodiments, a day may be 18 to 24 hours. In embodiments, a day may be 24 hours.

"Effective amount" or "pharmaceutically effective amount" of an agent as provided herein is meant to refer to a sufficient amount of an active ingredient to provide the desired therapeutic effect.

"Precision-timed" as used herein refers to the release of the component as an immediate release or delayed, immediate release. In embodiments, the term "release" is with respect to oral administration to the patient, wherein oral administration is time 0.

"Release component" or "component" as used herein refers to the element of the tablet that contains the API, e.g., buspirone, and non-active excipients. Each release component is separated by an erosion barrier. In embodiments, the first and second release components are layers. In embodiments, the third release component is a core that has one "outside" surface in contact with the inner erosion barrier.

It is to be noted that terms such as "first," "second," "third," "top," "bottom," "upper," "lower," are applied foremostly for purposes of clarity and distinguishing one element or object from another. Such terms, especially "top," "bottom," "upper," and "lower" are relative and dependent of the orientation of an object (e.g., tablet) which may be same as or different from the orientations of the same object presented in the figures provided herein.

Figure 1A:
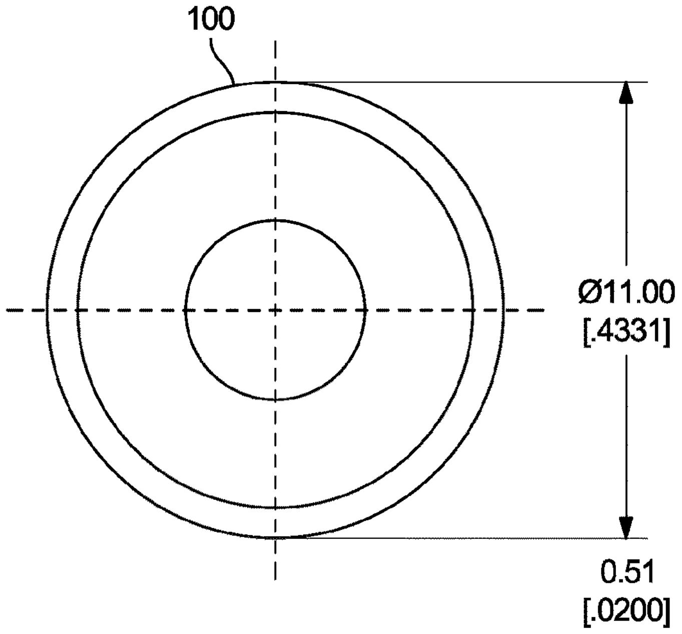
FIG. 1A is a top view of one embodiment of a trimodal, precision-timed release release tablet disclosed herein.
Figure 1B:
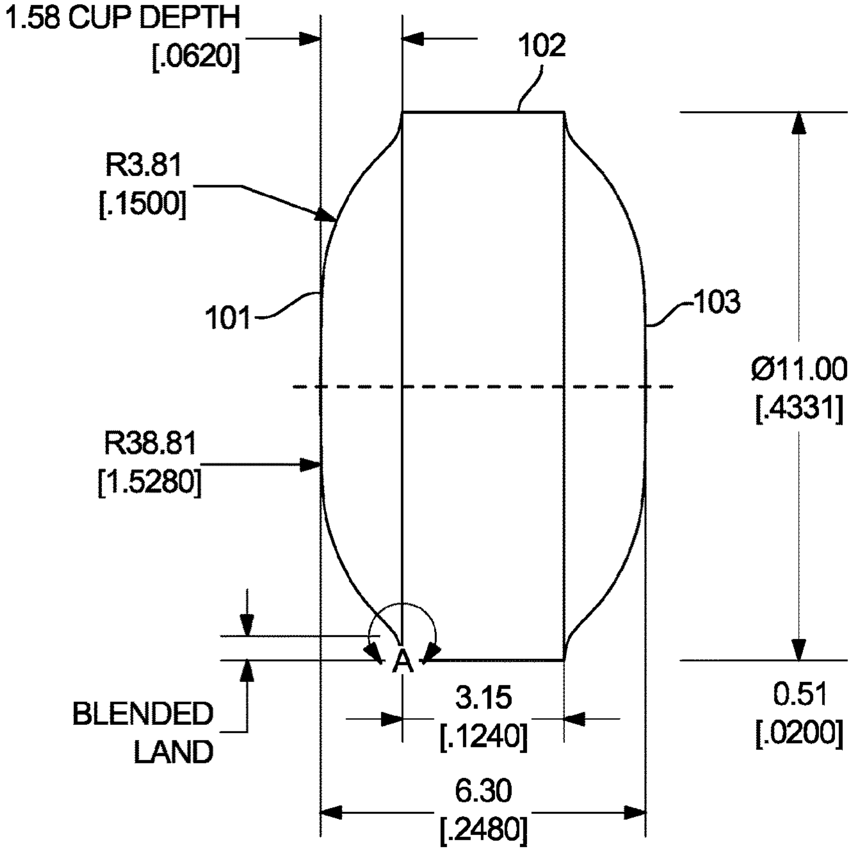
FIG. 1B is a perspective view of one embodiment of a trimodal, precision-timed release release tablet disclosed herein.

FIGS. 1A and 1B provide a top view and perspective view, respectively, of an embodiment of a tablet 100. FIG. 1A shows a round biconvex tablet. As shown in FIG. 1B, the tablet (100) includes a cylindrical central band section (102) or "belly bend" around the center of the tablet (100). The top (101) and bottom (103), oriented as left and right, respectively in FIG. 1B of the tablet (100) are shown as multiple radii convex sections, which provide the tablet (100) with a symmetrical appearance. As each convex section has the same features, any references to the structure of one convex section may be considered a reference to the other convex section, unless indicated otherwise. Each end of the convex section curves away from the band section (102) to a flat surface of the convex section. As shown in FIG. 1B, the portions of the first release component (104) identified as "blended land" are the flat section between the cup and the belly band. The size of the blended land helps with the structural integrity of the tablet. Without an appropriately sized "land" the compression forces across the erosion barrier layers would not be uniform and the relaxation force after compression could cause delamination/splitting and impact the release timing.

The diameter of the tablet (100) can be from about 9.00 mm to about 13.00 mm, or from about 10.00 mm to about 12.00 mm. In one embodiment, as shown in FIGS. 1A and 1B, the diameter is 11.00 mm.

The distance between the center of each convex section (i.e., the peak points A and B on the top (101) and bottom (103) of the tablet), which define the overall thickness of the tablet (100), is from about 5.00 mm to about 8.00 mm, or from about 6.00 mm to about 7.00 mm. In one embodiment, as shown in FIG. 1B, the distance between the peak points A and B is about 6.30 mm. The width of central band (102) can be from about 40% to about 60% of the distance between the peak points A and B, or from about 45% to about 55%, or about 50%. In one embodiment, as shown in FIG. 1B, the width of central band (102) is 50% of the distance between the peak points A and B, or 3.15 mm.

Figure 2:
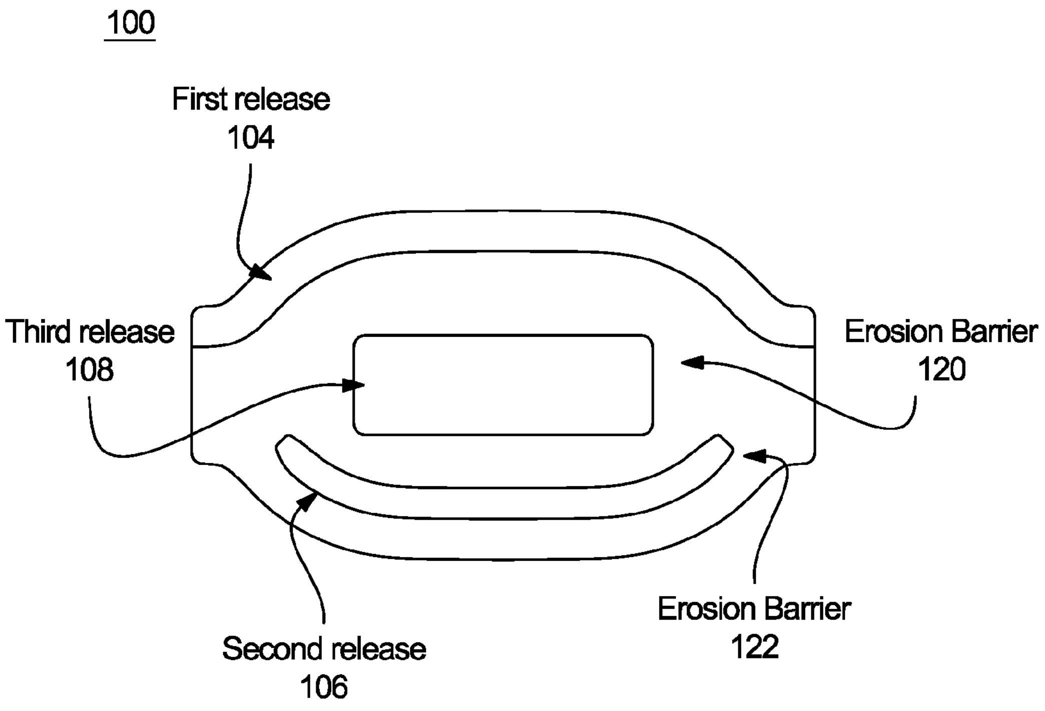
FIG. 2 is a cross-sectional diagram of one embodiment of a trimodal, precision-timed release release tablet disclosed herein.

As illustrated in FIG. 2, the tablet (100) can include three release components (104), (106), and (108), respectively, separated by erosion barrier layers (outer erosion barrier layer (120) and inner erosion barrier layer (122)). The three release components are located separate and apart from each other in the tablet (100); e.g., at specific and controlled positions within the tablet. As shown in FIG. 2, the first release component (104), containing a first precision-timed release of buspirone is positioned on the exterior, or on the top (101), of the tablet (100). Immediately beneath the first release component (104), unit is an outer erosion barrier layer (120). A second release component (106), containing a second precision-timed release of buspirone, is positioned between the outer erosion barrier layer (120) and an inner erosion barrier layer (122), such that the second release component (106) is completely surrounded by the outer and inner erosion barrier layers. A third release component (108), containing a third precision-timed release of buspirone is positioned at the center or core of the tablet. The inner erosion barrier layer (122) completely surrounds a third release component (108). As shown in FIG. 2, the release component is positioned between the first and third release components.

The first release component (104), is designed for release of a first precision-timed release of buspirone immediately following oral administration of the tablet (100) to a patient (i.e., immediate release or IR). The IR can be substantially complete within about 5 minutes to about 45 minutes after oral administration of the tablet to a patient or about 20 minutes to about 30 minutes after oral administration of the tablet to a patient. In one embodiment, the IR is substantially complete within 30 minutes after oral administration of the tablet to a patient. In this context, "substantially complete" can mean release of no less than 90% of the first precision-timed release.

The second and third release components (106) and (108) are designed for delayed release of the second and third precision-timed releases of buspirone, respectively. Although the second and third releases are delayed with respect to the first release component, each layer will be completely released in totality within 30 minutes. The delayed releases are achieved by the erosion barrier layers and positioning of the second and third release components within the tablet.

Since the first release component (104) is designed for immediate release of the first precision-timed release of buspirone, the first release component (104) is located on the exterior of the tablet (100), e.g., top (101). As a result, the first release component (104) is readily available for dissolution immediately after administration to a patient thereby releasing the first precision-timed release of buspirone. The bottom surface of the first release component is bordered by the outer erosion barrier layer (120).

The first release component is approximately 549-600 microns thick and covers the entire top surface of the tablet (100) following the contour of the outer tablet surface (101).

According to one embodiment, the first release component (104) releases from about 10% to about 50% of the total buspirone in the tablet, or from about 30% to about 40%, or about 33%.

The second release component (106) is a delayed, immediate release, designed for release of a second precision-timed release of buspirone that begins about 3 hours to about 6 hours following oral administration of the tablet to a patient. In an embodiment, release of the second precision-timed release of buspirone begins about 3 to about 5 hours following oral administration of the tablet to a patient. In an embodiment, release of the second precision-timed release of buspirone begins about 3.5 to about 4.5 hours following oral administration of the tablet to a patient. In an embodiment, release of the second precision-timed release of buspirone begins about 4 hours following administration of the tablet to a patient. The second release component may be approximately 549-750 microns thick.

According to certain embodiments, the second precision-timed release is from about 25% to about 45% of the total buspirone in the tablet, or from about 30% to about 40%. In one embodiment, the second precision-timed release is about 33% of the total buspirone in the tablet.

The third release component (108) is a delayed, immediate release, containing the third precision-timed release of buspirone can be positioned at the center of the tablet. The third release component is approximately 1.97-2.03 mm thick×4.95-5.05 mm in diameter with a flat-faced radius edge.

According to one embodiment, the third release component (108) includes a third precision-timed release of buspirone that is delayed in release until about 6 hours to about 12 hours following oral administration of the tablet to a patient. According to another embodiment, release of the third precision-timed release of buspirone begins about 6 hours to about 9 hours following oral administration of the tablet to a patient. According to another embodiment, release of the third precision-timed release of buspirone begins about 7 hours to about 8 hours following oral administration of the tablet to a patient. According to another embodiment, release of the third precision-timed release of buspirone is delayed until about 8 hours following oral administration of the tablet to a patient. The third precision-timed release of buspirone can be a delayed, immediate release precision-timed release.

According to one embodiment, the third precision-timed release is about 10% to about 40% of the total buspirone in the tablet (100), or from about 25% to about 35%, or from about 30% to about 35%. According to another embodiment, the third precision-timed release of buspirone can be about 33% of the total buspirone in the tablet.

The outer and inner erosion barrier layers (120) and (122), collectively referred to as the "erosion barrier layers," can have the same composition. Although the outer erosion barrier layer (120) and the inner erosion barrier layer (122) are shown as separate structures in FIG. 2, in embodiments where the erosion barrier layers have the same composition, there may not be a clear physical boundary or distinction between the erosion barrier layers in the finished tablet.

The outer and inner erosion barrier layers can each comprise glyceryl behenate, a blend of low-substituted hydroxypropyl cellulose (L-HPC) and hydroxypropyl cellulose. L-HPCs are insoluble in water and comprise a glucose backbone that is substituted to a minimal extent by hydroxypropyl groups. This chemistry prevents dissolution of the L-HPCs but they swell in the presence of water. In certain embodiments, the erosion barrier layers can comprise two or more grades of L-HPCs, such as LH-21 and LH-32. LH-21 is moderately fibrous and has a mean particle size of 45 μm. LH-21 has a molecular weight of around 120,000 and a hydroxypropyl content of around 11%. LH-32 is micronized, with a mean particle diameter of 20 μm. LH-32 has a molecular weight of 115,000 and a hydroxypropyl cellulose content of 8%.

In one embodiment, the outer and inner erosion barrier layers each comprise about 30% to about 50% by weight of glyceryl behenate, 35% to about 45% of glyceryl behenate or about 37.5% to about 42.5% of glyceryl behenate. In one embodiment, the glyceryl behenate can be COMPRITOL® ATO 888.

The outer and inner erosion barrier layers can each comprise about 40% to about 60% total by weight of two or more grades of L-HPC, or about 45% to about 55% or about 47.5% to about 52.5%. In one embodiment, the outer and inner erosion barrier layers each comprise about 15% to about 25% by weight of a first grade of L-HPC, such as LH-21, and about 25% to about 35% by weight of a second grade of L-HPC, such as LH-32; about 20% to about 23% by weight of LH-21 and about 27.5% to about 32.5% by weight of LH-32.

The outer and inner erosion barrier layers can each comprise about 4% to about 8% by weight of hydroxypropyl cellulose. In certain embodiments, the outer and inner erosion barrier layers can each comprise about 5% to about 7% by weight of hydroxypropyl cellulose. In certain embodiments, the hydroxypropyl cellulose of the outer and inner erosion barrier layers can be hydroxypropyl cellulose Type L.

The erosion barrier layers may further include silicon dioxide, for example, colloidal silicon dioxide such as AEROSIL® 200 Pharma. In certain embodiments, the outer and inner erosion barrier layers each comprise about 1% or less by weight of colloidal silicon dioxide, about 0.2%-0.8% by weight of colloidal silicon dioxide or about 0.2% to 0.6% by weight of colloidal silicon dioxide.

The precision-timed release profile of the tablet described, result, in part, from the composition of the outer and inner erosion barrier layers. The erosion barrier layer (EBL) comprises a combination of a waxy excipient, glyceryl dibehenate, and a blend of three disintegrants that are different iterations of low-substituted hydroxypropyl cellulose (L-HPC). Glyceryl dibehenate is an inert compound that is non-water soluble and has minimal chemical interactivity with water. In contrast, L-HPC is water soluble and will rapidly swell when in contact with water. Because of the manufacturing compression processes the particles in the EBL are tightly packed, which limits liquid permeation into the EBL matrix. When the surface particles come in contact with a liquid medium they swell, the surface weakens, and the particles shed off of the tablet. A "fresh" layer of particles becomes exposed, and the process is repeated until the underlying API layer is exposed and released.

In certain embodiments, the trimodal, precision-timed release tablet includes about 200-300 mg of the outer erosion barrier layer, about 225-275 mg, about 230-260 mg, or about 235-245 mg. In certain embodiments, the precision-timed release tablet includes about 100-150 mg of the inner erosion barrier layer, about 115-135 mg or about 120-130 mg.

In certain embodiments, the thickness of the outer erosion barrier layer is about 574-888 microns.

In certain embodiments, the thickness of the inner erosion barrier layer is about 862-1071 microns.

The distance between the first and third release components (104, 108) is about 1,436-1,906 microns. As shown in FIG. 2, the distance between the first and third release components (104, 108) is about 1,567-1,932 microns.

Similarly, the distance between the second and third release components (106, 108) is about 862-1071 microns. As shown in FIG. 2, the distance between the second and third release components (106, 108) is about 862-1071 microns.

In certain embodiments, each release component contains, in addition to the dosage material, an excipient and a diluent. The amount of excipient and diluent in each release component depends on the total amount of buspirone in the tablet. Exemplary excipients include croscarmellose sodium, microcrystalline cellulose, and magnesium stearate.

In certain embodiments, the first release component can contain from about 15% w/w to about 25% w/w of buspirone. In one embodiment, the first release component can contain about 75% w/w to about 85% w/w of excipient including croscarmellose sodium, microcrystalline cellulose, magnesium stearate, sodium starch glycolate, and colloidal silicon dioxide.

In certain embodiments, the second release component can contain about 15% w/w to about 25% w/w of buspirone. In one embodiment, the second release component can contain about 75% w/w to about 85% w/w of excipient including croscarmellose sodium, microcrystalline cellulose, magnesium stearate, sodium starch glycolate, and colloidal silicon dioxide.

In certain embodiments, the third release component can contain about 15% w/w to about 25% w/w of buspirone. In one embodiment, the third release component can contain about 75% w/w to about 85% w/w of excipient including croscarmellose sodium, microcrystalline cellulose, magnesium stearate, sodium starch glycolate, and colloidal silicon dioxide.

The tablets disclosed herein are suitable for the delivery of an effective amount of at least one anxiolytic and salts thereof. At least one other active ingredient may be combined with the anxiolytic in a single release component within the tablet, or one or more release components within the tablet may comprise the additional active ingredient. Salts of the active ingredients used in conjunction with the present tablets may be obtained commercially or can be prepared using standard procedures known to those skilled in the art of synthetic organic chemistry. The anxiolytic provided herein may be in the form of a pharmaceutically acceptable salt, prodrug, or other derivative or active metabolite. According to a particular embodiment, the anxiolytic is buspirone or a pharmaceutically acceptable salt thereof. According to another embodiment, the anxiolytic is buspirone hydrochloride.

Optional components present in the trimodal, precision-timed release tablet can include, but are not limited to, additional binders, lubricants, disintegrants, stabilizers, surfactants, coloring agents, coatings, and diluents. Suitable diluents include, but are not limited to, dicalcium phosphate dihydrate, lactose, cellulose, kaolin, mannitol, sodium chloride, dry starch, hydrolyzed starches, silicon dioxide, titanium oxide, alumina, talc, microcrystal-line cellulose, and powdered sugar. Suitable binder materials include, but are not limited to, starch (including corn starch and pregelatinized starch), gelatin, sugars (including sucrose, glucose, dextrose, lactose and sorbitol), polyethylene glycol, waxes, natural and synthetic gums (e.g., acacia, tragacanth, sodium alginate, polyvinylpyrrolidone, celluloses, and Veegum), and synthetic polymers such as polymethacrylates and polyvinylpyrroli-done. Suitable lubricants include, but are not limited to, magnesium stearate, calcium stearate, stearic acid, and polyethylene glycol. Suitable disintegrants include, but are not limited to, starches, clays, celluloses, algins, gums, or crosslinked polymers. Suitable surfactants include, but are not limited to, those containing carboxylate, sulfonate and sulfate ions, associated with cations such as sodium, potassium and ammonium ions; long alkyl chain sulfonates and alkyl aryl sulfonates such as sodium dodecylbenzene sulfonate; dialkyl sodium sulfosuccinates, such as sodium bis-(2-ethylhexyl)-sulfosuccinate; and alkyl sulfates such as sodium lauryl sulfate. Nontoxic auxiliary substances such as wetting or emulsifying agents, pH buffering agents, and preservatives may also be included in the tablet or in the individual drug-containing release components.

In one embodiment, the trimodal, precision-timed release tablet is a film-coated tablet. Suitable film coatings include aqueous film coatings, such as OPADRY® II (Colorcon, Inc., Harleysville, PA).

The trimodal, precision-timed precision-timed release tablet described herein can be useful in a method of treatment of a disorder, condition or disease for which an anxiolytic is generally indicated by administering the trimodal, precision-timed release tablet to a patient in need thereof. In one embodiment, the disorder, condition or disease is anxiety or anxiety related dosorders.

The trimodal, precision-timed release tablet described herein can be useful in methods for extending the therapeutic duration of buspirone by administering the tablet to a patient in need thereof. As a result of the proportioned trimodal release of buspirone, the therapeutic duration of buspirone is effective for longer than 12 hours, at least 14 hours, and up to the entire day, after oral administration of the tablet to a patient.

The trimodal, precision-timed release tablets described herein can be manufactured through a series of tablet-within-a-tablet compression operations. For example, the third release component is compressed and then surrounded by or covered with the inner erosion barrier layer. The second release component is then compressed on top of the inner erosion barrier layer and then surrounded by or covered with the outer erosion barrier layer. The first release component is then compressed on top of the outer erosion barrier layer. In another embodiment, the second release component is compressed on the bottom of the inner erosion barrier layer, such that the third release component is positioned between the first release component and the second release component.

Example 1

A trimodal, precision-timed release tablet, such as those illustrated in FIGS. 1A, 1B and 2, may be manufactured with the apparatus and steps as provided herein. The precision-timed release tablet may include a total of 30 mg of buspirone. The three release components of the trimodal, precision-timed release tablet may have the following composition:

| Release layer | Ingredient | % (w/w) |
|---|---|---|
| First Release layer | buspirone | 15%-25% |
| | croscarmellose sodium | 1%-4% |
| | microcrystalline cellulose | 65%-78% |
| | magneisum stearate | 0.5%-1.5% |
| | sodium starch glycolate | 2.0%-6% |
| | colloidal silicon dioxide | 0.25%-0.75% |
| Second Release layer | buspirone | 15%-25% |
| | croscarmellose sodium | 1%-4% |
| | microcrystalline cellulose | 65%-78% |
| | magneisum stearate | 0.5%-1.5% |
| | sodium starch glycolate | 2.0%-6% |
| | colloidal silicon dioxide | 0.25%-0.75% |
| Third Release layer | buspirone | 15%-25% |
| | croscarmellose sodium | 1%-4% |
| | microcrystalline cellulose | 65%-78% |
| | magneisum stearate | 0.5%-1.5% |
| | sodium starch glycolate | 2.0%-6% |
| | colloidal silicon dioxide | 0.25%-0.75% |

The first release component contains a first precision-timed release of buspirone that is about 33% of the total buspirone dose in the tablet. The second release component contains a second precision-timed release of buspirone that is about 33% of the total buspirone dose in the tablet. The third release component contains a third precision-timed release of buspirone that is about 33% of the total buspirone dose in the tablet.

In an embodiment, each of the three release components of the trimodal, precision-timed release tablet may have the following composition:

| IR Layer Components | Function | % (w/w) | mg/IR layer |
|---|---|---|---|
| Buspirone | Active Ingredient | 20.000 | 10.000 |
| Croscarmellose sodium | Filling Agent | 2.000 | 1.000 |
| Microcrystalline cellulose | Filling Agent | 72.500 | 36.250 |
| Magnesium Stearate | Flow regulating agent | 1.000 | 0.500 |
| Sodium starch glycolate | Disintegrant | 4.000 | 2.000 |
| Colloidal silicon dioxide | Glidant | 0.500 | 0.250 |
| Total | | | 50.000 |

The outer and inner erosion barrier layers have the following composition:

| Ingredient | Percentage (by weight) |
|---|---|
| Glyceryl behenate (COMPRITOL ® 888) | 35%-45% |
| L-HPC LH-21 | 15%-25% |
| L-HPC LH-32 | 25%-35% |
| HPC Type L | 4%-8% |
| Colloidal silicon dioxide (AEROSIL ® 200 Pharma) | ≤1% |

The trimodal, precision-timed release tablet is structured generally as shown in FIG. 2. The three release components are incorporated at specific and controlled positions within the tablet. The first release component is positioned as a surface of the tablet and on an outer erosion barrier layer. The second release component is positioned between the outer erosion barrier layer and an inner erosion barrier layer. The third and final release component is positioned at the center of the tablet and surrounded by the inner erosion barrier layer. The tablet includes 240 mg of the outer erosion barrier layer and 125 mg of the inner erosion barrier layer.

While the present invention has been described in detail, the present invention is not limited to the foregoing embodiments described above. Modifications may be made without departing from the concept of the present invention.

The invention claimed is:

1. A trimodal, precision-timed release tablet for oral administration of buspirone or pharmaceutically acceptable salt thereof comprising:

(a) a first release component comprising (i) about 15% w/w to about 25% w/w of buspirone as a first precision-timed release, wherein about 10% to about 50% of the total buspirone in the tablet is released at time zero following oral administration of the tablet to a patient (ii) about 1% w/w to about 4% w/w of croscarmellose sodium, (iii) about 65% w/w to about 78% w/w of microcrystalline cellulose, (iv) about 0.5% w/w to about 1.5% w/w of magnesium stearate (v) about 2.0% w/w to about 6% w/w of sodium starch glycolate; and (vi) about 0.25% w/w to about 0.75% w/w of colloidal silicon dioxide;

(b) a second release component comprising (i) about 15% w/w to about 25% w/w of buspirone as a second pulse of about 30% to about 40% of the total buspirone in the tablet released beginning from about 3 to about 6 hours following oral administration of the tablet to a patient, (ii) about 1% w/w to about 4% w/w of croscarmellose sodium, (iii) about 65% w/w to about 78% w/w of microcrystalline cellulose, (iv) about 0.5% w/w to about 1.5% w/w of magnesium stearate (v) about 2.0% w/w to about 6% w/w of sodium starch glycolate; and (vi) about 0.25% w/w to about 0.75% w/w of colloidal silicon dioxide; and (c) a third release component comprising (i) about 15% w/w to about 25% w/w of buspirone as a third precision-timed release of about 10% to about 40% of the total buspirone in the tablet released about 6 to about 12 hours following oral administration of the tablet to a patient, (ii) about 1% w/w to about 4% w/w of croscarmellose sodium, (iii) about 70% w/w to about 80% w/w of microcrystalline cellulose, (iv) about 0.5% w/w to about 1.5% w/w of magnesium stearate (v) about 2.0% w/w to about 6% w/w of sodium starch glycolate; and (vi) about 0.25% w/w to about 0.75% w/w of colloidal silicon dioxide; and, wherein the tablet is structured such that the first release component is positioned as a surface of the tablet and on an outer erosion barrier layer, the second release component is positioned between the outer erosion barrier layer and an inner erosion barrier layer such that it is surrounded by the outer and inner erosion barrier layers, and the third release component is positioned at the center of the tablet and surrounded by the inner erosion barrier layer.

2. The tablet of claim 1, wherein the first release component releases about 33% of the total buspirone in the tablet.

3. The tablet of claim 1, wherein the second release component releases about 33% of the total buspirone in the tablet.

4. The tablet of claim 1, wherein the third release component releases about 33% of the total buspirone in the tablet.

5. The tablet of claim 1, wherein release of the second precision-timed release begins about 3 to about 5 hours following oral administration of the tablet to a patient.

6. The tablet of claim 1, wherein release of the third precision-timed release begins about 7 to about 9 hours following oral administration of the tablet to a patient.

7. The tablet of claim 1, wherein the outer and inner erosion barrier layers each further comprise about 35% to about 45% by weight of glyceryl behenate, about 15% to about 25% by weight of LH-21, about 25% to about 35% by weight of LH-32, and about 4% to about 8% by weight of hydroxypropyl cellulose Type L.

8. The tablet of claim 7, wherein the outer and inner erosion barrier layers each further comprise about 1% or less by weight of colloidal silicon dioxide.

9. The tablet of claim 1, wherein the outer and inner erosion barrier layers each further comprise about 37.5% to about 42.5% by weight of glyceryl behenate, about 20% to about 23% by weight of LH-21, about 27.5% to about 32.5% by weight of LH-32, and about 5% to about 7% by weight of hydroxypropyl cellulose Type L.

10. The tablet of claim 1, wherein the first release component is about 600 microns thick, the second release component is about 750 microns thick and the third release component is about 2.03 mm thick with a flat-faced radius edge.

11. The tablet of claim 1, wherein the third release component is positioned between the first release component and the second release component.

12. The tablet of claim 1, wherein:

the total buspirone dose of the tablet is 30 mg;

the first release component comprises 17.5% w/w to 23.0% w/w of buspirone, and 77.0% w/w to 82.5% w/w cumulatively of croscarmellose sodium, microcrystalline cellulose, magnesium stearate, sodium starch glycol ate, and colloidal silicon dioxide;

the second release component comprises 17.5% w/w to 23.0% w/w of buspirone and 77.0% w/w to 82.5% w/w cumulatively of croscarmellose sodium, microcrystalline cellulose, magnesium stearate, sodium starch glycol ate, and colloidal silicon dioxide; and the third release component comprises 17.5% w/w to 23.0% w/w of buspirone and 77.0% w/w to 82.5% w/w cumulatively of croscarmellose sodium, microcrystalline cellulose, magnesium stearate, sodium starch glycol ate, and colloidal silicon dioxide.

13. A method for extending the therapeutic duration of buspirone, the method comprising administering the tablet of claim 1 to a patient in need thereof, wherein the therapeutic duration of the buspirone is effective for at least 14 hours after oral administration of the tablet to a patient.

14. A method of treatment of a disorder, condition, or disease for which buspirone is generally indicated, the method comprising administering the tablet of claim 1 to a patient in need thereof.

15. The method of claim 14, wherein the disorder, condition, or disease is a generalized anxiety disorder or anxiety related disorders.

* * * * *